United States Patent
Fackler et al.

(10) Patent No.: US 12,006,517 B2
(45) Date of Patent: Jun. 11, 2024

(54) METHOD FOR PURIFICATION OF BACTERIOPHAGE PARTICLES

(71) Applicant: Adaptive Phage Therapeutics, Inc., Gaithersburg, MD (US)

(72) Inventors: Joseph Robert Fackler, Gaithersburg, MD (US); Carl Merril, Bethesda, MD (US); Jarrar Haider, Columbia, MD (US); Viet Dang, Port Republic, MD (US)

(73) Assignee: Adaptive Phage Therapeutics, Inc., Gaithersburg, MD (US)

( * ) Notice: Subject to any disclaimer, the term of this patent is extended or adjusted under 35 U.S.C. 154(b) by 0 days.

(21) Appl. No.: 17/571,645

(22) Filed: Jan. 10, 2022

(65) Prior Publication Data
US 2022/0127583 A1   Apr. 28, 2022

Related U.S. Application Data

(63) Continuation of application No. PCT/US2020/053602, filed on Sep. 30, 2020.

(60) Provisional application No. 62/908,943, filed on Oct. 1, 2019.

(51) Int. Cl.
*C12N 7/00* (2006.01)
*A61K 35/76* (2015.01)
*A61P 31/04* (2006.01)
*B01D 61/20* (2006.01)
*B01D 69/08* (2006.01)

(52) U.S. Cl.
CPC ............... *C12N 7/00* (2013.01); *A61K 35/76* (2013.01); *A61P 31/04* (2018.01); *B01D 61/20* (2013.01); *B01D 69/08* (2013.01); *B01D 2311/2676* (2013.01); *B01D 2311/2688* (2013.01); *B01D 2315/10* (2013.01); *C12N 2795/10132* (2013.01); *C12N 2795/10151* (2013.01); *C12N 2795/10232* (2013.01); *C12N 2795/10251* (2013.01); *C12N 2795/10332* (2013.01); *C12N 2795/10351* (2013.01)

(58) Field of Classification Search
None
See application file for complete search history.

(56) References Cited

U.S. PATENT DOCUMENTS

| 2007/0010001 A1 | 1/2007 | Bujanover |
| 2010/0075398 A1 | 3/2010 | Mathers et al. |
| 2011/0008873 A1 | 1/2011 | Lipinski et al. |
| 2011/0300528 A1 | 12/2011 | Jassim et al. |
| 2015/0247127 A1 | 9/2015 | Robert |
| 2020/0157644 A1 | 5/2020 | Rames |
| 2022/0056421 A1 | 2/2022 | Gagnon et al. |
| 2023/0106864 A1 | 4/2023 | Holder et al. |

FOREIGN PATENT DOCUMENTS

| CN | 112175915 A | 1/2021 |
| EP | 2117568 A1 | 11/2009 |
| PL | 212286 B1 | 1/2012 |
| WO | 2008/071774 A1 | 6/2008 |
| WO | 2013022717 A1 | 2/2013 |
| WO | 2013138716 A1 | 9/2013 |
| WO | 2021/174066 A1 | 9/2021 |

OTHER PUBLICATIONS

International Search Report and Written Opinion with Search Strategy dated Mar. 22, 2021 and received in PCT/US20/53602.
Schooley et al., "Development and Use of Personalized Bacteriophage-Based Therapeutic Cocktails to Treat a Patient with a Disseminated Resistant Acinetobacter baumannii Infection", Antimicrobial Agents and Chemotherapy, vol. 61, Iss. 10, pp. 1-14 (2017).
Van Belleghem et al., "*Revised* A Comparative Study of Different Strategies for Removal of Endotoxins from Bacteriophage Preparations", Journal of Microbiological Method, vol. 132, pp. 153-159 (2016).
Van Belleghem et al., "A Comparative Study of Different Strategies for Removal of Endotoxins from Bacteriophage Preparations", Journal of Microbiological Method, vol. 132, pp. 153-159 (2016).
Official Communication issued for the corresponding EP Patent Application No. 20792880.5 dated May 11, 2022.
Transmittal and International Preliminary Report on Patentability dated Apr. 5, 2020 received in PCT/US2020/53602.
Chinese Office Action and Search Report with English language translation issued Mar. 7, 2024 in corresponding CN application No. 202080067232.2, 20 pages.
Hietala, V. et al., "The Removal of Endo- and Enterotoxins From Bacteriophage Preparations", Frontiers in Microbiology, vol. 10(1674) Jul. 2019, 9 pages.
Luong, T. et al., "Rapid Bench to Bedside Therapeutic Bacteriophage Production", Methods in Molecular Biology, vol. 2734, 2024, pp. 67-88.

*Primary Examiner* — Nicole Kinsey White
(74) *Attorney, Agent, or Firm* — Edell, Shapiro & Finnan, LLC

(57) ABSTRACT

A method of recovering viable phage from, for example, a crude phage preparation such as a lysate resulting from amplification of phage in bacterial cell culture is disclosed. The method may be "universal"; that is, applicable to the purification of a broad range of phage species and strains. The phage product resulting from the method may have an acceptably low endotoxin titer (e.g. less than 500 EU/ml) and sufficiently high phage titer (e.g. $>1\times10^9$ PFU/ml) for use in therapeutic applications.

19 Claims, No Drawings

METHOD FOR PURIFICATION OF BACTERIOPHAGE PARTICLES

CROSS-REFERENCE TO RELATED APPLICATIONS

This application is a Continuation of PCT/US20/53602 filed on Sep. 30, 2020, which claims priority to U.S. Provisional Application 62/908,943 filed on Oct. 1, 2019, both of which are hereby incorporated by reference in their entirety.

BACKGROUND OF THE INVENTION

Field of the Invention

The invention relates to a method of recovering viable phage from, for example, a crude phage preparation such as a lysate resulting from amplification of phage in bacterial cell culture. The method may be "universal"; that is, applicable to the purification of a broad range of phage species and strains.

Discussion of the Related Art

In the following discussion, certain articles and methods will be described for background and introductory purposes. Nothing contained herein is to be construed as an "admission" of prior art. The Applicant(s) expressly reserve the right to demonstrate, where appropriate, that the articles and methods referenced herein do not constitute prior art under the applicable statutory provisions.

Multiple drug resistant (MDR) bacteria are emerging at an alarming rate. Currently, it is estimated that at least 2 million infections are caused by MDR organisms every year in the United States leading to approximately 23,000 deaths. Moreover, it is believed that genetic engineering and synthetic biology may also lead to the generation of additional highly virulent microorganisms.

For example, *Staphylococcus aureus* are Gram positive bacteria that can cause skin and soft tissue infections (SSTI), pneumonia, necrotizing fasciitis, and blood stream infections (i.e. bacteremias). Methicillin-resistant *S. aureus* ("MRSA") is an MDR organism of great concern in the clinical setting as MRSA is responsible for over 80,000 invasive infections, close to 12,000 related deaths, and is the primary cause of hospital acquired infections. Additionally, the World Health Organization (WHO) has identified MRSA as an organism of international concern.

In view of the potential threat of rapidly occurring and spreading virulent microorganisms and antimicrobial resistance, alternative clinical treatments against bacterial infection are being developed. One such potential treatment for MDR infections involves the use of phage. Bacteriophages ("phages") are a diverse set of viruses that replicate within and can kill specific bacterial hosts. The possibility of harnessing phages as an antibacterial agent was investigated following their initial isolation early in the loth century, and they have been used clinically as antibacterial agents in some countries with some success. Notwithstanding this, phage therapy was largely abandoned in the United States after the discovery of penicillin, and only recently has interest in phage-based therapies been renewed.

The successful therapeutic use of phage relies on the viable production of phage compositions suitable for administration to a patient (e.g. a patient suffering from an infection by an MDR bacterial pathogen), and thereby necessarily having high phage titers (i.e. a high phage content). Producing phage in such high numbers (e.g. "amplification") for therapeutic application requires growth in a bacterial host cell culture. This, however, means that the phage lysate obtained from the culture will contain host cell materials (e.g. host cell proteins (HCPs), cell wall materials and residual DNA (rDNA)) which are incompatible with use in a composition intended for therapeutic use. In particular, among the host cell wall materials will be, in the case of Gram-negative bacteria (e.g. *Escherichia coli* host cells), endotoxins (also known as lipopolysaccharides (LPS) and lipoglycans), which can cause significant toxicity and illness in patients, and therefore must be substantially removed from therapeutic compositions (e.g. to levels of less than 500 or 1000 EU/ml). That is, the phage must be subjected to a procedure so as to produce a "phage product" that has been sufficiently purified or otherwise "cleansed" of host cell materials and other contaminants, so that it may be used, or adapted for use, as a therapeutic composition.

Previously, purification of phage has been performed by ion-exchange chromatography and/or isopycnic centrifugation on a cesium chloride (CsCl) gradient. Ion-exchange chromatography facilitates separation of biomolecules (such as phage) based on the affinity of the biomolecules to the ion exchange resin (Andriaenssens E M et al., *Virology* 434(2): 265-270, 2012). While this procedure works well with charged proteins, each unique phage requires optimization of the chromatography conditions needed to capture and elute the phage. As such, this approach to purification becomes cumbersome for commercial production of therapeutic phage compositions given the amount of work required to optimize the conditions for each phage species or strain, which can also be further complicated by batch to batch fluctuations in buffer/growth media conditions from the phage amplification stage. On the other hand, isopycnic centrifugation on a CsCl density gradient does not require such troubleshooting, but is time consuming, not readily scalable and presents other problems. For example, endotoxins and HCPs can bind to the phage resulting in multiple bands of phage and a loss in titer. The Applicant(s) have also observed that some phage species and strains do not survive this purification process.

Accordingly, there is a need to develop viable alternative procedures for recovering or preparing phage intended for use in phage therapy. Preferably, such procedures would be "universal"; that is, applicable for the purification of a broad range of phage species and strains. Further, alternative procedures would preferably be suitable for use in recovery systems capable of processing large volumes in a relatively rapid manner, such as continuous or single process filtration-type systems including Tangential Flow Filtration (TFF) systems (also known as cross-flow filtration).

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in any accompanying drawings and defined in the appended claims.

The Applicant(s) sought to identify and develop a phage recovery method which advantageously benefits from the relatively limited particle size range of phage (i.e. the particles of phage of most species and strains range in size from 24 to 200 nm in length), and which might therefore underpin a purification method that may be universal or, at least, applicable to the purification of a significant number of phage of therapeutic significance. As such, the method of the invention employs selective filtration to retain phage particles, while enabling unwanted materials such as endotoxins, HCPs and residual host cell DNA to be freely washed through the filter so that they may be removed. However, this relied on the identification of a process for dissociating unwanted materials (i.e. contaminants) from the phage particles and breaking up (disaggregating) any large aggregations of unwanted materials (especially endotoxins which are known to form large aggregations (micelles) through their hydrophobic lipid regions), without substantially damaging or denaturing the phage (i.e. so that there is little or no loss of viable phage). As described hereinafter, and exemplified in the Examples, the Applicant(s) have indeed identified a phage recovery method that is capable of reliably recovering phage from host cell materials (particularly endotoxins) following large scale phage amplification in culture that, to date, has been successful with all phage species and strains tested.

The invention relates to a method of recovering viable phage from a crude phage preparation, wherein the method comprises the steps of:

1) Adding the crude phage preparation to an active filtration system comprising a size exclusion filter, wherein said filter comprises a pore size smaller than a size of the phage contained within the crude phage preparation;

2) Passing a series of buffers over the filter, wherein said series of buffers comprise:

a) a buffer that disrupts ionic protein interactions;

b) a buffer that disrupts hydrophobic/hydrophilic interactions; and c) a buffer that precipitates the phage; and 3) Recovering said phage from the filter, wherein said recovered phage are viable.

The method is suited to being performed in an active filtration system such as a continuous filtration system (e.g. TFF).

The "phage product" resulting from the method of the invention may have an acceptably low endotoxin titer (e.g. less than 500 EU/ml) and high phage titer (e.g. greater than $1\times10^9$ PFU/ml) for therapeutic application. As such, the phage product may be suitable for use in, or for the preparation of compositions comprising phage for use in, a phage therapy for treating a bacterial infection.

The invention therefore also relates to a phage product prepared in accordance with the method of the invention.

Further, the invention relates to a therapeutic composition comprising a phage product prepared in accordance with the method of the invention, optionally in combination with one or more pharmaceutically acceptable excipient, carrier, buffer and/or diluent.

Still further, the invention relates to a method of phage therapy of a bacterial infection in a patient (particularly a method of treating a bacterial infection in a patient), said method comprising administering to the patient phage purified in accordance with the method of the invention or a therapeutic composition as defined above.

DETAILED DESCRIPTION

The following definitions are provided for specific terms which are used in the following written description.

Definitions

As used in the specification and claims, the singular form "a", "an" and "the" include plural references unless the context clearly dictates otherwise. Also, as understood by one of skill in the art, the term "phage" can be used to refer to a single phage or more than one phage.

The present invention can "comprise" (open ended) or "consist essentially of" the components of the invention. As used herein, "comprising" means the elements recited, or their equivalent in structure or function, plus any other element or elements which are not recited. The terms "having" and "including" are also to be construed as open ended unless the context suggests otherwise.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term "about" means within an acceptable error range for the particular value, such as ±1-20%, preferably ±1-10% and more preferably ±1-5%. In even further embodiments, "about" should be understood to mean+/−5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by one of ordinary skill in the art. This includes, at very least, the degree of expected experimental error, technique error and instrument error for a given technique used to measure a value.

Where used herein, the term "and/or" when used in a list of two or more items means that any one of the listed characteristics can be present, or any combination of two or more of the listed characteristics can be present. For example, if a composition is described as containing characteristics A, B, and/or C, the composition can contain A feature alone; B alone; C alone; A and B in combination; A and C in combination; B and C in combination; or A, B, and C in combination.

The term "bacteriophage" or "phage", as understood by one of ordinary skill in the art, refers to a non-cellular infective agent that reproduces only in a suitable host cell, that is, a bacterial host cell.

As used herein, "phage therapy" refers to any therapy to treat a bacterial infection or bacterial-caused disease, which may involve the administration to a subject requiring treatment (e.g. a patient) of one or more therapeutic composition that can be used to infect, kill or inhibit the growth of a bacterium, which comprises one or more viable phage as an antibacterial agent (e.g. a composition comprising one phage strain or a phage "cocktail") and which may further comprise, or otherwise be administered in combination with a further therapeutic composition comprising, one or more antibiotics, one or more bactericides, and/or one or more other therapeutic molecules such as small molecules or biologics that have bactericidal activity. Where more than one therapeutic composition is involved in the phage therapy, then the compositions may have a different host range (e.g. one may have a broad host range and one may have a narrow host range, and/or one or more of the compositions may act synergistically with one another). Further, as understood by one of ordinary skill in the art, the therapeutic composition(s) used in a phage therapy will also typically comprise a range of inactive ingredients selected from a variety of conventional pharmaceutically acceptable excipients, carriers, buffers, and/or diluents. The term "pharmaceutically acceptable" is used to refer to a non-toxic material that is compatible with a biological system such as a cell, cell culture, tissue, or organism. Examples of pharmaceutically acceptable excipients, carriers, buffers, and/or diluents are familiar to one of skill in the art and can be found, e.g. in *Remington's Pharmaceutical Sciences* (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water and saline.

The term "active filtration system" is to be understood as referring to a filtration system wherein the material to be filtered (i.e. a feed fluid) contacts the filter under a constant or variable applied pressure and is not merely filtered under the force of gravity (i.e. such that the feed fluid is "pushed" through the filter). Typically, an active filtration system comprises a pump to provide the feed material at a suitable desired pressure. Particular examples of active filtration systems are known to one of ordinary skill in the art as continuous filtration systems. The method of the invention is particularly well suited to being conducted in a continuous filtration system, however batch-wise active filtration systems may also be employed.

The term "continuous filtration system" will be understood as referring to filtration systems wherein the feed is continuously recirculated "ahead" of the filter and arranged to continually "wash away" any "filter cake" (which can block passage through the filter). Particular examples of such systems include Tangential Flow Filtration (TFF) systems (also known as cross-flow filtration systems). TFF systems are typically operated with some back pressure from a back pressure control (BPC) valve, which pressure pushes a feed fluid through the filter along with contaminants (which forms the "permeate" or "waste"). Feed fluid remaining ahead of the filter is recirculated (and, if desired, added to with new feed fluid). The BPC valve can be adjusted (i.e. to increase or decrease pressure) to compensate for fluctuations as material is processed through the TFF system.

The invention relates to a method of recovering viable phage that is suitable for use in the preparation of compositions comprising phage for use in phage therapy. The method may be "universal"; that is, applicable for the recovery of a broad range of phage species and strains.

More particularly, the invention relates to a method of recovering viable phage from a crude phage preparation, wherein the method comprises the steps of:
1) Adding the crude phage preparation to an active filtration system comprising a size exclusion filter, wherein said filter comprises a pore size smaller than a size of the phage contained within the crude phage preparation;
2) Passing a series of buffers over the filter, wherein said series of buffers comprise:
   a) a buffer that disrupts ionic protein interactions;
   b) a buffer that disrupts hydrophobic/hydrophilic interactions; and
   c) a buffer that precipitates the phage; and
3) Recovering said phage from the filter, wherein said recovered phage are viable.

The crude phage preparation will typically be a lysate resulting from amplification of phage (such as a phage obtained and/or selected from phage "stocks" or a library of phage stocks) in a bacterial cell culture. Such amplification of phage in a bacterial cell culture may be conducted in accordance with, for example, any of the standard techniques known to one of ordinary skill in the art (e.g. standard techniques described in Sambrook J et al., *Molecular Cloning: A laboratory manual*, Cold Spring Harbor Lab. Press, Plainview, NY), including small- or large-scale liquid culture of a suitable bacterial host (e.g. *E. coli* bacteria (EcoIII)). The recovery method of the invention is, however, suitable and intended for large-scale culture (i.e. "large batch amplification"). The crude phage preparation may be pre-processed to remove large contaminants with a clarification process (e.g. centrifugation to remove large cellular debris) and/or filtration through a porous filter membrane (e.g. a 0.22 μM) or other size exclusion filter and/or depth filter, and/or by using one or more perfusion technique such as those that will be apparent to one of ordinary skill in the art.

In some embodiments, the phage in the crude phage preparation will be a phage of therapeutic significance; that is, a phage that is suitable for use in phage therapy. Thus, for example, the phage in the crude phage preparation may be a phage suitable for use in phage therapy of a patient suffering from an infection by a bacterial pathogen that poses a serious health threat including, but not limited to *E. coli*, the "ESKAPE" pathogens (i.e. *Enterococcus faecium, Staphylococcus aureus, Klebsiella pneumonia, Acinetobacter baumannii, Pseudomonas aeruginosa* and *Enterobacter* sp) and/or a MDR bacteria (i.e. bacteria that demonstrate resistance to multiple antibacterial drugs, e.g. antibiotics) including, but not limited to, methicillin-resistant *S. aureus* (MRSA), vancomycin-resistant Enterococci (VRE) and (ESBL)-producing Enterobacteriaceae which are resistant to ceftriaxone and fluoroquinolones.

In step 1) of the method, the crude phage preparation is added to an active filtration system comprising a size exclusion filter. Suitable size exclusion filters are known to one of ordinary skill in the art and include, for example, polymeric and fibrous membranes, molecular sieves and filters including hollow fiber filters (e.g. modified polyether sulfone (mPES) hollow fiber filters). The size exclusion filter retains the phage particles present in the crude phage preparation. In some preferred embodiments, the size exclusion filter will preferably be selected to retain material present in the crude phage preparation that has a molecular weight of at least 100 kDa, more preferably at least 150 kDa, 200 kDa, 20 kDa or 300 kDa, even more preferably at least 350 kDa or 400 kDa, and most preferably at least 450 kDa or 500 kDa. In other words, the size exclusion filter will preferably be selected to allow contaminant material of less than 100 kDa, more preferably less than 150 kDa, 200 kDa, 250 kDa or 300 kDa, even more preferably less than 350 kDa or 400 kDa, and most preferably less than 450 kDa or 500 kDa, to pass through the filter and thereby be removed from the crude phage preparation to produce a concentrated phage preparation. Thus, in some preferred embodiments, the size exclusion filter is one having a molecular weight cut-off (MWCO) in the range of about 100 to about 500 kDa. Such size exclusion filters may therefore be provided with a pore size that permits passage of materials of a size less than 100 kDa, less than 150 kDa, less than 200 kDa, less than 250 kDa, less than 300 kDa, less than 350 kDa, less than 400 kDa, less than 450 kDa, less than 500 kDa, less than 550 kDa, less than 600 kDa, less than 650 kDa, less than 700 kDa, less than 750 kDa, or less than 800 kDa.

As demonstrated in the examples, the tested shear rate performed was maintained <3000 sec$^{-1}$. This shear rate may be higher, with preferred shear rates of no more than 6000 sec$^{-1}$. In preferred embodiments, the shear rates range from 1-3000 sec$^{-1}$, 2000-4000 sec$^{-1}$, 3000-5000 sec$^{-1}$, 4000-6000 sec$^{-1}$, 6000-8000 sec$^{-1}$, 1000-4000 sec$^{-1}$, 2000-5000 sec$^{-1}$, 3000-6000 sec$^{-1}$, 4000-7000 sec$^{-1}$, 5000-8000 sec$^{-1}$, 1000-6000 sec$^{-1}$, 2000-6000 sec$^{-1}$, 3000-6000 sec$^{-1}$, 4000-6000 sec$^{-1}$, 5000-7000 sec$^{-1}$, 6000-8000 sec$^{-1}$, less than 2000 sec$^{-1}$, less than 3000 sec$^{-1}$, less than 4000 sec$^{-1}$, less than 5000 sec$^{-1}$, less than 6000 sec$^{-1}$, less than 7000 sec$^{-1}$ or less than 8000 sec$^{-1}$.

Also as demonstrated in the examples, the Transmembrane Pressure (TMP) was set to 2.5 psi and did not exceed 5 psi. In preferred embodiments, the TMP ranges from 1.5 psi to 2.0 psi, 2.0 psi to 2.5 psi, 2.5 psi to 3.0 psi, 2.5 psi to 3.5 psi, 2.5 psi to 4.0 psi, 2.5 psi to 4.5 psi, 2.5 psi to 5.0 psi, 3.0 psi to 3.5 psi, 3.0 psi to 4.0 psi, 3.0 psi to 4.5 psi, or 3.0 psi to 5.0 psi. In further preferred embodiments, the psi is set to 1.5 psi, 2.0 psi, 2.5 psi, 3.0 psi, 3.5 psi, 4.0 psi, 4.5 psi, or 5 psi.

In step 2) of the method, a series of buffers are passed over the filter. The buffers may assist to dissociate contaminants from phage particles and/or disaggregate any aggregations of contaminants that may be present, in a manner wherein substantially the majority of the phage remain viable. By dissociating contaminants from phage particles and/or disaggregating any aggregations of contaminants that may be present in the phage preparation, the method enables removal of these unwanted materials by the size exclusion filter. The buffers employed in step 2) comprise: a) a buffer that disrupts ionic protein interactions; b) a buffer that disrupts hydrophobic/hydrophilic interactions; and c) a buffer that precipitates the phage.

In some embodiments, the buffer a) that disrupts ionic protein interactions comprises a high ionic strength buffer such as a buffer having an ionic strength in the range of 250 to 950 mM, more preferably 500 to 650 mM (e.g. a solution of at least 250 mM, at least 300 mM, at least 350 mM, at least 400 mM, at least 450 mM, at least 500 mM, at least 550 mM, at least 600 mM, at least 650 mM, at least 700 mM, at least 750 mM, at least 800 mM, at least 850 mM, at least 900 mM, or at least 950 mM 1M salt, such as sodium chloride and/or magnesium chloride).

In some embodiments, the buffer b) that disrupts hydrophobic/hydrophilic interactions comprises a suitable detergent (e.g. a non-ionic surfactant such as a polyoxyethylene derivative (e.g. Triton™ X-100, polysorbate 20 (Tween 20) or polysorbate 80 (Tween 80)) and/or a zwitterionic surfactant such as lauryldimethylamine oxide (LDAO)) and/or a non-denaturing organic solvent (e.g. ethanol, butanol, glycerol or dimethyl sulfoxide (DMSO)) and/or chaotropic agent (e.g. guanidine hydrochloride (GuHCl; Wilson M J et al., *J Biotechnol.* 88(1):67-75, 2001), thiourea and urea).

In some embodiments, the buffer b) comprises a non-ionic surfactant selected from Triton x-100 and polysorbate 20. Triton X-100 and polysorbate 20 have a micelle molecular weight of about 90 kDa and 98 kDa respectively and, therefore, may readily pass through a size exclusion filter with a pore size permitting passage of materials less than 100 kDa for example (i.e. a MWCO of 100 kDa).

In some preferred embodiments, the buffer b) comprises:
(i) Triton X-100;
(ii) Triton X-100 and a second detergent (e.g. a zwitterionic surfactant such as LDAO);
(iii) Triton X-100 and a high ionic strength solution;
(iv) Triton X-100 and a chaotropic agent; or
(v) a chaotropic agent.

In some other preferred embodiments, the buffer b) comprises:
(vi) a zwitterionic surfactant and a high ionic strength solution; or
(vii) a zwitterionic surfactant and a chaotropic agent.

One particularly preferred embodiment of buffer b) comprises 1-2% (v/v) Triton X-100+500 mM NaCl.

In some embodiments, the buffer c) that precipitates the phage comprises any of the standard agents for precipitating large biomolecules such as phage known to one of ordinary skill in the art, and which will not substantially damage or denature the phage (i.e. so that substantially the majority of the phage remain viable). One particularly suitable agent for precipitating the phage is a saturated solution of ammonium sulfate (i.e. $(NH_4)_2SO_4$). This has been found to still be effective in active filtration systems. Indeed, the Applicant(s) have found that precipitation of the phage with a precipitating agent such as $(NH_4)_2SO_4$ is particularly well suited to continuous type filtration systems such as TFF inasmuch as the system enables an even, gradual, increase in $(NH_4)_2SO_4$ concentration leading to reliable and even precipitation of phage particles. This can also prevent the phage from forming large aggregates which can block passage of contaminants through a size exclusion filter. Further, in the context of TFF, precipitating the phage in the TFF system means that the phage recovery can be achieved from a closed sterile environment and without the need for centrifugation which can lead to loss of phage.

Thus, in some preferred embodiments, the buffer c) is an ammonium sulfate buffer. However, alternatively, the buffer c) may be a sodium sulfate ($Na_2SO_4$) buffer or magnesium sulfate ($MgSO_4$) buffer. Mixtures of such agents may also be suitable (e.g. $(NH_4)_2SO_4$ and $MgSO_4$). Further, in some embodiments, the buffer c) may comprise a chaotropic agent such as GuHCl.

In some embodiments, the method further comprising adding an endonuclease capable of degrading DNA or RNA. For example, endonucleases such as a DNAase, a RNAase or benzonase, can be added to the method to cleave double-stranded DNA, single stranded DNA or single stranded RNA. In some preferred embodiments, the endonuclease is added to the crude phage preparation. Additionally, the endonuclease can be added during the method as an additional step and/or can also be added to the recovered phage in solution to remove any residual nucleic acid.

The buffers a), b) and c), but especially buffers a) and b), in step 2) of the method, may be passed over the filter in any order. Also, each or any of buffers a), b) and c) may be passed over the filter one or more times. Further, where any two or more of the buffers a), b) and c) are passed over the filter more than once, than the numbers of time that the individual buffers are passed over the filter may be the same or different. For example, in some embodiments, a buffer a) may be passed over the filter, followed by two passes of a buffer b) which may be the same or different and which may be optionally separated by a wash step (e.g. using phosphate buffered saline (PBS) such as 1×PBS), and thereafter, buffer c) passed over the filter to precipitate the phage. One or more wash step(s) (e.g. using 1×PBS) may be performed between any or all of buffers a), b) and c). Further, one or more wash step(s) may be performed after a final pass of buffer c) over the filter so as to remove or reduce any remaining buffer c) (e.g. $(NH_4)_2SO_4$) and resolubilize the phage particles (e.g. by using 5-10 volumes of ix PBS or another buffer suitable for administration to a patient).

The Applicant(s) have found that not only does the step 2) enable the dissociation of contaminants from phage particles and/or the disaggregation of any aggregations of contaminants (so as to thereby enable removal of these unwanted materials), the high ionic strength solution(s) stabilizes the phage particles and contribute to the success of the method in obtaining purified viable phage.

The step 3) of the method enables the "recovery" of the precipitated phage. Where the method is conducted using a continuous filtration system such as TFF, the phage recovery can be readily achieved from the closed sterile environment "ahead" of the filter and without the need for centrifugation which can lead to loss of phage (e.g. by recovering the phage into a reservoir and pumping/pipetting the recovered phage from the reservoir). Nevertheless, in some embodiments, recovered viable phage may be subjected to a centrifugation step.

The recovered viable phage or "phage product" may be tested for contaminants (in particular, tested for residual endotoxins using a standard Limulus Amebocyte Lysate (LAL) assay) and, if desired, re-subjected to one or more of the steps of the method of the invention. Where re-subjected to at least an additional step of filtering with a size exclusion filter, then the size exclusion filter may be substituted with one with a higher MWCO if desired.

The method of the invention may be operated so as to regularly, or more preferably continuously or substantially continuously, monitor for the removal of contaminants (especially endotoxins) from the phage preparation. For example, material passing through the filter in step 2) (i.e. the permeate), may be assessed for endotoxins by, for example, a standard LAL assay. Additionally or alternatively, the permeate may be analyzed by standard spectrophotometric techniques known to one of ordinary skill in the art, so as to detect changes in absorbance at 210/254 nm (endotoxins), 260 nm (HCPs) and 280 nm (residual DNA). The use of a continuous filtration system such as TFF lends itself to "real time" monitoring by enabling frequent sampling and analysis of the permeate. Indeed, commercially available systems exist (e.g. the Konduit system by Spectrum Labs (Repligen; <https://www.repligen.com/>) which can be set up to automatically monitor the progress of the purification method of the invention in the context of a continuous filtration system such as TFF. That is, the Konduit system was designed to automate TFF processing by monitoring UV absorbance at 260 nm and 280 nm as well as conductivity. Thus, rather than using the Konduit system to automate TFF, the system could be adapted to monitor for the removal of contaminants from crude phage preparations as the method of the invention is conducted. An additional sensor could also be applied to test for absorbance at 210/254 nm so as enable the detection of endotoxins in the permeate.

The recovered viable phage resulting from the method of the invention may have an acceptably low endotoxin titer (e.g. less than 500 EU/ml) and total host cell protein level (e.g. less than or equal to 100 µg/mL), and a high phage titer (e.g. greater than $0.5 \times 10^8$ PFU/ml, but preferably greater than $1 \times 10^8$ PFU/ml or $0.5 \times 10^9$ PFU/ml, and more preferably greater than $1 \times 10^9$ PFU/ml) for therapeutic application. As such, the recovered viable phage may be suitable for use in, or for the preparation of compositions comprising phage for use in, a phage therapy for treating a bacterial infection. Prior to use in phage therapy, the recovered viable phage may be subjected to a step of exchanging the buffer of the recovered viable phage with a buffer suitable for administration to a patient (especially by IV administration).

In some embodiments, the recovered viable phage has an endotoxin titer of less than 1 EU/ml, less than 100 EU/ml, less than 200 EU/ml, less than 300 EU/ml, less than 400 EU/ml, less than 500 EU/ml, less than 600 EU/ml, less than 700 EU/ml, less than 800 EU/ml, less than 900 EU/ml, or less than 1000 EU/ml.

Typically, regulatory authorities such as the Food and Drug Administration (FDA) require that a human patient undergoing administration of a therapeutic composition which may be likely to include endotoxin contaminants receive endotoxins at a rate of no more than 5 EUs per kg of body weight per hour of intravenous (IV) administration. Therefore, based on the average weight of adults (89.7 kg and 77.3 kg for men and women respectively), the average male adult can receive ~450 EU per hour and the average female adult can receive ~385 EU per hour. A medical practitioner will be able to readily formulate viable phage recovered according to the method of the invention at the patient's bedside to ensure that the maximal amounts of endotoxins are not exceeded.

The invention also relates to a phage product prepared in accordance with the method of the invention.

Further, the invention also relates to a therapeutic composition comprising a phage product prepared in accordance with the method of the invention, optionally in combination with one or more pharmaceutically acceptable excipient, carrier, buffer and/or diluent.

Such a composition may comprise one or more phage types (e.g. one or more phage strain(s) including phage obtained from phage "stocks"); that is, the composition may comprise a phage "cocktail". In addition, the composition may optionally further comprise, for example, one or more antibiotics, one or more bactericides, and/or one or more other therapeutic molecules such as small molecules or biologics that have bactericidal activity.

In some embodiments, the therapeutic composition will be suitable for therapeutic use such as, for example, but not limited to: IV administration, intraarticular, intrathecal administration, topical application (including intraocular), and/or nebulization to a patient.

Still further, the invention also relates to a method of phage therapy of a bacterial infection in a patient (particularly a method of treating a bacterial infection in a patient), said method comprising administering to the patient phage purified in accordance with the method of the invention or a therapeutic composition as defined above.

Treatment may be any treatment and therapy, whether of a human or an animal (e.g. in veterinary applications), in which some desired therapeutic effect is achieved, for example, the inhibition or delay of the progress of a bacterial infection, and includes a reduction in the rate of progress of the bacterial infection, a halt in the rate of its progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a subject susceptible to or at risk of the occurrence or re-occurrence of the bacterial infection may be treated as described herein. Such treatment may prevent or delay the occurrence or re-occurrence of the infection in the subject. Or like other antibiotics, administration of the recovered viable phage could be given, prophylactically to a patient prior, for example, who is about to undergo dental work or surgery.

Administration in vivo can be affected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

Further use could include industrial applications such as environmental disinfection, such as, for example, in building water systems and hospital rooms and surfaces.

More specifically, the recovered viable phage can be used to remove and/or prevent the growth of bacteria on surfaces, floors and counters (e.g., such as in food preparation areas or medical facilities), medical devices (including but not limited to, stents, catheters, intubation tubes, or ventilator equipment), other moist and warm environments (e.g., such as showers, water and sewage pipes), cooling or heating water systems, (e.g., cooling towers), marine engineering systems (e.g., such as, for example, pipelines of the offshore oil and gas industry), pipes, boat hulls, as a handwash to help eliminate spread of virulent bacteria by health workers, patients and others. Additional industrial uses can include coating of implantable medical devices, part of machinery used in industrial processes, a culvert, a pool used in a waste water treatment facility, waste water treatment facility, industrial fluid handling machinery, a wound, within the body, a medical process, agricultural processes, and/or machinery.

Even further use could include applications in biotechnology such as but not limited to phage display and pathogen testing.

Even further use could include applications could include use in food production such as but not limited to pathogen control on crops in farming and/or disinfection of food.

Although the invention herein has been described with reference to embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLE(S)

The invention will now be further illustrated with reference to the following example(s). It will be appreciated that what follows is by way of example only and that modifications to detail may be made while still falling within the scope of the invention.

Example 1

Recovery of EcCH79Φ79 Bacteriophage from Large Scale *E. coli* Culture

The recovery of the *E. coli* bacteriophage EcCH79Φ79 was undertaken as follows. This bacteriophage has a particle size of length of 74±<1 nm and width of 55±2 nm with a typical Podoviridae morphology.

Large Batch Amplification and Initial Filtration

The host *E. coli* strain was grown in 25 mL of tryptic soy broth (TSB) growth media at 37° C. in a shaking incubator overnight. The overnight culture was used to seed each of two 4 L flasks containing 1.8 L of TSB media incubated at 37° C. with shaking at 175 RPM. Bacterial growth was monitored every hour via spectrophotometric methods. Once mid-log phase growth of the culture was achieved ($OD_{600}$ ~0.1), both of the large batch cultures were infected with EcCH79Φ79 phage stock from plate lysate amplification at a Multiplicity of Infection (MOI) of ~0.0025. Both flasks were re-incubated at 37° C. with shaking at 175 RPM. Culture viability was monitored at 1-hour intervals for detection of lysis. Once a dramatic drop in $OD_{600}$ was detected, corresponding to cellular lysis, both large batch cultures were harvested for clarification. Both large batch flasks were pooled, and large cellular debris removed via centrifugation. The supernatant was collected and sequentially filtered through 0.88 μm, 0.45 μm and 0.22 μm filters. The filtrate was pooled into two autoclaved glass bottles and stored at 4° C. for further processing.

Tangential Flow and Filtration (TFF) Setup, Sanitization and Operation

The TFF used in this example was the KR2i TFF system (Repligen). The KR2i TFF system utilized a single use flow path assembled with Pharmapure 25 tubing, Pressure Transducers and equipped with 300 kDa molecular weight cut-off (MWCO), modified polyether sulfone (mPES), hollow fiber filter (S04-E300-05-N) with a surface area of 1600 $cm^2$. The entire flow path was sanitized with 0.1 M NaOH followed by neutralization with 1×PBS.

The TFF operating parameters were tracked in real-time by the manufacturer's software system. General parameters or "best practices" for operation are as follows:

Shear rate is maintained <3000 1/seconds.

Transmembrane Pressure (TMP) set to 2.5 psi and not exceeding 5 psi.

Operators can adjust settings of the instrument (Flow Rate, TMP, etc.) as needed to fall within best practices guidelines. During the purification cycle, each wash step is measured in diavolumes (DV). A diavolume is equal to the volume of the lysate being washed. For example: If the lysate contained in the TFF is 200 mL, then a wash of 2×DV consists of 400 mL of washing buffer.

Initial Concentration of Lysate

The collected and sequentially filtrate ("filtered lysate") was loaded into the reservoir of the TFF system as a continuous fed batch. Under these conditions, the lysate was continuously fed into the processing reservoir while being filtered against the 300 kDa MWCO filter. This allowed the lysate to be fed into the system and concentrated at the same time.

During this initial concentration, removal of impurities <300 kDa was observed, and the remaining phage were concentrated to a processing volume between ~200-400 mL. Endotoxins were also concentrated by a factor of ~10×.

Purification Cycle

Upon completion of the initial concentration, the concentrated lysate was subjected to the following purification cycle:

High ionic salt wash (500 nM sodium chloride)—The concentrated lysate was initially washed with a high ionic strength salt, namely 500 mM NaCl. This initial wash served two purposes; first, to promote disassociation of endotoxins from the phage by increasing salt concentrations and, secondly, to remove growth media and smaller proteins from the lysate. During this process, the bulk of the growth media (TSB) was removed along with broken/disassociated proteins.

Detergent wash (Triton X-100)—Following the high ionic salt wash, the lysate was then washed with a non-ionic detergent, TX-100, to remove free and bound endotoxins from the phage. Since TX-100 is not compatible as a pharmaceutical excipient, it was removed by washing the system with 4×DV washes with 1×PBS buffer.

Phage Precipitation

Precipitation of the phage was performed within the TFF system to reduce loss of phage titer during centrifugation and increase the removal efficiency of endotoxins. Briefly, the phage was precipitated by washing the product with 5×DV of a saturated solution of $(NH_4)_2SO_4$. As the concentration of ammonium sulfate increased, the proteins (phage) precipitated out and the material in both the reservoir and in the filter connections became noticeably cloudy. By slowly increasing the concentration of $(NH_4)_2SO_4$ within the high ionic strength and/or detergent washes, it was found that while aggregates were formed (i.e. the precipitated phage), large aggregates of the phage that would block passage through the hollow fiber filter can be avoided. Upon completion of the precipitation stage, the purified phage product was washed with 10 DV of 1×PBS to remove $(NH_4)_2SO_4$ and solubilize the phage aggregates.

Quantification of Phage

Bacteriophage present in the lysate during the course of the purification method and in the final phage product (i.e. the phage product following the 1×PBS wash) was quantified using standard full plate titer or spot titer methods as briefly described below:

Full plate titer method—Active phage particles (i.e. viable phage) or Plaque Forming Units (PFUs) was measured by serially diluting the lysate or phage product in SM buffer or PBS 1:10 to cover dilutions $10^{-1}$ thru $10^{-8}$. A fresh culture of the host bacterial strain was then aliquoted into the number of tubes corresponding to the number of dilutions to be plated. An additional tube was also prepared to serve as a bacterial control plate. An aliquot of phage from each dilution was then added to each tube containing the host cell culture, and then incubated at 37° C. for 10-18 min to allow attachment of phage to host cells. After incubation, 2.5 mL of molten soft agar was pipetted into each tube and decanted across the surface of separate TSA plates. Once solidified, the plates were incubated at 37° C. overnight or until lawn formation. Plates with countable plaques (30-300) were scored and averages of duplicate plates were used in conjunction with the corresponding dilution factor to determine the final phage titer.

Spot Titer Method—The lysate or phage product were serially diluted in SM buffer or PBS 1:10 such to cover dilutions $10^{-1}$ thru $10^{-8}$. A fresh culture of the host bacterial strain was then aliquoted into the number of tubes corresponding to the number of dilutions to be plated. An additional tube was also prepared to serve as a bacterial control plate. 2.5 mL of molten soft agar was pipetted into each tube and decanted across the surface of separate TSA plates. Once solidified, 10 μL of each dilution of phage was spotted onto each plate in triplicate or sextuplicate and allowed to dry. Once spots had dried, the plates were incubated at 37° C. overnight or until lawn formation. Plates with countable plaques were scored and averages of duplicate plates were used in conjunction with the corresponding dilution factor to determine the final phage titer.

Endotoxin Testing

Endotoxin levels present in the lysate during the course of the purification method and in the final phage product was measured using the commercially-available Limulus Amebocyte Lysate (LAL) Turbidimetric Kit with the Pyros Kinetix Flex Incubating Kinetic Tube Reader (Associates of Cape Cod, Inc. <www.acciusa.com/>). Assays were performed according to the manufacturer's instructions and/or recommendations.

The results of the phage recovery are shown in Table 1.

TABLE 1

Production Data: EcCH79Φ79

| Purification Stage | $V_{Total}$ (mL) | Phage Titer | | | | Endotoxin Titer | | | |
|---|---|---|---|---|---|---|---|---|---|
| | | PFU/mL | $PFU_{Total}$ | Log ($PFU_{Total}$) | Log Dif. | EU/mL | $EU_{Total}$ | Log ($EU_{Total}$) | Log Dif. |
| Initial filtrate (from large batch culture) | 3212.4 | — | — | — | — | 4.80E+04 | 1.54E+08 | 8.19 | — |
| High ionic strength wash (4 × 500 mM NaCl) | 343.4 | 4.20E+09 | 1.44E+12 | 12.16 | — | 5.00E+06 | 1.72E+09 | 9.23 | −1.05 |
| Detergent wash (2 × 1% TX-100 + 500 mM NaCl) | 346.9 | 2.17E+10 | 7.53E+12 | 12.88 | −0.72 | 2.18E+03 | 7.56E+05 | 5.88 | 3.36 |
| Phage precipitation (($NH_4)_2SO_4$)* | 327.4 | 4.27E+09 | 1.40E+12 | 12.15 | 0.73 | 0.00E+00 | 0.00E+00 | NA | NA |
| Wash to remove residual $(NH_4)_2SO_4$ (4 × PBS) | 254.7 | 5.10E+10 | 1.30E+13 | 13.11 | −0.97 | 5.27E+02 | 1.34E+05 | 5.13 | 0.75 |

*Sample was diluted ~1:3 during dialysis to remove excess salt.

The initial wash with 500 mM NaCl showed no significant change in total endotoxins. This was likely the result of disaggregation of the endotoxins from phage particles and/or other protein contaminants, but with little to no actual removal from the lysate. However, after the wash with 1% TX-100, the endotoxin titer dropped by 99.57% (2.37-logs), and this was followed by a further slight reduction in endotoxins from the ammonium sulfate precipitation (see Table 1).

Ammonium sulfate causes interference in the measurement of both the phage titer and endotoxin assays. Therefore, to quantify the samples, a small volume was loaded into gamma-irradiated dialysis cassettes (ThermoFisher) and dialyzed against 1×PBS to remove residual salt prior to testing. It was found that after the final PBS wash, the phage titer increased to $1.3 \times 10^{13}$ PFUs, a 90% increase, which was likely the result of freeing phage particles from contaminants. The final endotoxin titer of the purified "phage product" was 527 EU/mL, a 3-log reduction in total endotoxin from the purification method.

Additional wash steps could be applied to the phage product to further reduce endotoxins. Moreover, the phage product may also be diluted in an appropriate buffer to a level below the recommended tolerance (5.0 EU/kg of body weight) of a patient or average adult weight. This would allow for the preparation of a high titer therapeutic phage composition (>$1 \times 10^9$ PFU/mL) with low endotoxin content (see Table 1). Notably, no centrifugation (which can result in loss of phage) was required for the recovery of the phage following precipitation.

Example 2

Recovery of EcCH27Φ38 Bacteriophage from Large Scale *E. coli* Culture

The recovery of the *E. coli* bacteriophage EcCH27Φ38 was undertaken as follows. This bacteriophage has a particle size of length of 73±4 nm and width of 59±3 nm with a typical Podoviridae morphology.

Large Batch Amplification and Initial Filtration

The host bacterial strain was grown as described in Example 1. Once mid-log phase growth of the culture was achieved ($OD_{600}$ ~0.4), the large batch cultures were infected with the EcCH27Φ38 phage stock from plate lysate amplification at a MOI of 0.0025. The flasks were then re-incubated as described in Example 1, and as soon as a dramatic drop in $OD_{600}$ was detected, the cultures were pooled, and large cellular debris is removed via centrifugation. The supernatant was collected and sequentially filtered in the same manner at that described in Example 1. The filtrate was pooled and stored at 4° C. for further processing.

Tangential Flow and Filtration (TFF) Setup, Sanitization and Operation

The TFF system, sanitization and operation was as described in Example 1. As such, the TFF flow path was equipped with a 300 kDa molecular weight cut-off (MWCO), modified polyether sulfone (mPES), hollow fiber filter (S04-E300-05-N) with a surface area of 1600 $cm^2$.

Initial Concentration of Lysate

The filtrate ("filtered lysate") was loaded into the reservoir of the TFF as a continuous fed batch. As such, the lysate was continuously fed into the processing reservoir while being filtered against the 300 kDa MWCO filter. During this initial concentration of the lysate, impurities of <300 kDa were removed. The phage were also concentrated to a processing volume of between ~200-400 mL.

Purification Cycle

Upon completion of the initial concentration, the concentrated lysate was subjected to the following purification cycle:

High ionic salt wash (500 nM NaCl/1×PBS)—The concentrated lysate was initially washed with a high ionic strength salt, in this case 500 mM NaCl in 1×PBS was used. During this process, it was observed that the bulk of the growth media (TSB) was removed along with broken/disassociated proteins.

Detergent wash (Triton X-100+500 mM NaCl/1×PBS)—Following the high ionic salt wash, the lysate was then washed with 1% TX-100+500 mM NaCl/1×PBS solution. The TX-100 and NaCl was subsequently removed by washing the lysate with 4×DV of 1×PBS buffer. Afterwards, it was noticed that there was some residual foaming from the detergent indicating that some follow up washes, or a repeat of the purification cycle, was needed to remove residual TX-100. In any case, in this example, the purification cycle was repeated so as to further reduce endotoxins.

Phage Precipitation

Precipitation of the phage was performed within the TFF system to reduce loss of phage titer during centrifugation and increase the removal efficiency of endotoxins. Briefly, the phage was precipitated by washing the product with 3×DV of a saturated solution of $(NH_4)_2SO_4$. As the concentration of ammonium sulfate increased, the proteins (phage) precipitated out and the material in both the reservoir and in the filter connections became noticeably cloudy. By slowly increasing the concentration of $(NH_4)_2SO_4$ within the high ionic strength and/or detergent washes, it was found that while aggregates were formed (i.e. the precipitated phage), large aggregates of the phage that would block passage through the hollow fiber filter can be avoided. Upon completion of the precipitation stage, the purified phage product was washed with 5 DV of 1×PBS to remove $(NH_4)_2SO_4$ and solubilize the phage aggregates.

Quantification of Phage

Bacteriophage present in the lysate during the course of the purification method and in the final phage product (i.e. the phage product following the 1×PBS wash) was quantified in the manner described in Example 1.

Endotoxin Testing

Endotoxin levels present in the lysate during the course of the purification method and in the final phage product were measured as described in Example 1.

The results of the recovery are shown in Table 2.

TABLE 2

| | | | | | | | | | |
|---|---|---|---|---|---|---|---|---|---|
| Production Data: EcCH2$_{7\Phi_3}$8 | | | | | | | | | |
| Purification | $V_{Total}$ | Phage Titer | | | | Endotoxin Titer | | | |
| Stage | (mL) | PFU/mL | PFU$_{total}$ | Log (PFU$_{total}$) | Log Dif. | EU/mL | EU$_{Total}$ | Log (EU$_{total}$) | Log Dif. |
| Large batch culture | 3600 | — | — | — | — | — | — | — | — |
| Initial filtrate (from large batch culture) | 250 | 6.68E+10 | 1.67E+13 | 13.22 | N/A | 1.61E+06 | 4.03E+08 | 8.6o | N/A |

TABLE 2-continued

Production Data: EcCH2$_{7\Phi 3}$8

| Purification Stage | $V_{Total}$ (mL) | Phage Titer | | | | Endotoxin Titer | | | |
|---|---|---|---|---|---|---|---|---|---|
| | | PFU/mL | PFU$_{total}$ | Log (PFU$_{total}$) | Log Dif. | EU/mL | EU$_{Total}$ | Log (EU$_{total}$) | Log Dif. |
| High ionic strength wash (4 × 500 mM NaCl) | 247 | 5.50E+09 | 1.36E+12 | 12.13 | 1.09 | 1.31E+06 | 3.24E+08 | 8.51 | 0.09 |
| First detergent wash (2 × 1% TX-100 + 500 mM NaCl) | 244 | 6.25E+10 | 1.53E+13 | 13.18 | −1.05 | 2.26E+04 | 5.51E+06 | 6.74 | 1.77 |
| Wash to remove TX-100 (4 × PBS) | 241 | 2.78E+10 | 6.70E+12 | 12.83 | 0.35 | 1.86E+04 | 4.48E+06 | 6.65 | 0.09 |
| Second detergent wash (2 × 1% TX-100 + 500 mM NaCl) | 238 | 5.83E+10 | 1.39E+13 | 13.14 | −0.31 | 6.85E+02 | 1.63E+05 | 5.21 | 1.44 |
| Wash to remove TX-100 (4 × PBS) | 235 | 9.00E+09 | 2.12E+12 | 12.33 | 0.81 | <1.00E+04 | <2.35E+06 | <6.37 | −1.16* |
| Phage precipitation (3 × saturated (NH$_4$)$_2$SO$_4$) | 232 | 3.60E+10 | 8.35E+12 | 12.92 | −0.59 | <1.00E+02 | <2.32E+04 | <4.37 | 2.00* |
| Wash to remove residual (NH$_4$)$_2$SO$_4$ (5 × PBS) | 229 | 6.00E+09 | 1.37E+12 | 12.14 | 0.78 | 3.29E+01 | 7.53E+03 | 3.88 | 0.49* |

*Values were estimated based on the largest value obtained from assay results.

As was also observed in Example 1, the initial wash with 500 mM NaCl showed no significant change in total endotoxins. However, after 2×DV wash with 1% TX-100+500 mM NaCl, the endotoxin titer dropped 98.3% (1.77 log), and this was followed by an additional 98.4% (1.44 log) drop after the second TX-100+500 mM NaCl wash (see Table 2). An additional 2-log reduction in endotoxin levels was achieved with the ammonium sulfate precipitation of the phage.

Some loss in phage titer was observed across the purification method in this example. That is, after the final PBS wash, the phage titer had decreased from 3.6×10$^{10}$ PFU/mL to 6×10$^9$ PFU/mL (see Table 2). The decrease in titer could be explained by loss of phage during the resuspension of precipitated phage. A second possibility is that the decrease in titer is the result of phage aggregates failing to breakup after the PBS washes.

The purification method achieved a final endotoxin titer of 32.9 EU/mL, nearly a 5-log reduction in total endotoxins. At this titer, the phage product does not require additional purification or dilution to achieve an acceptable endotoxin titer for use as a composition for phage therapy. Also, while the phage titer did drop, it is still sufficiently high for therapeutic application (>1×10$^9$ PFU/mL). Notably, in this example, no centrifugation (which can result in loss of phage) was required for the recovery of the phage following precipitation.

Example 3

Purification of Additional Bacteriophage from Large Scale Cultures

Including the EcCH79Φ79 and EcCH27Φ38 of Examples 1 and 2, fourteen (14) unique phage strains have to-date been successfully purified according to the method of the invention. Purification of these phage collectively represent at least three (3) known phage morphologies, and cover seven (7) species of host bacteria (see Table 3 below). For all twenty-eight (28) bacteriophage tested to-date, the phage particles were successfully purified, "survived" the purification method and were viable. The results indicate that the purification method of the invention provides a universal phage purification method (i.e. provides a method that ought to be successfully applicable over a broad range of phage species and strains) and suitable for the preparation of compositions comprising phage for use in phage therapy.

In additional test runs, the purification method has shown a stepwise reduction of endotoxin, host cell proteins, and residual DNA (data not shown). Reduction of each of these contaminants has been demonstrated in the purification of a S. aureus phage, SaWIQ0488Φ1. In this batch a 3.6 L filtered batch lysate was processed through the purification cycle including a 10× concentration step. The bulk filtered material had an endotoxin concentration that was above the upper range of the assay yielding >12500 EU/mL (>4.5×10$^7$ total EU). After purification, the endotoxin concentration was reduced to 667 EU/mL (2.5×10$^5$ EUs total) for at least a 2.3 log reduction in total EU. The HCP concentration measured in the in the batch lysate was above the upper range of the assay, yielding >810 ng/mL (>2.9×10$^6$ ng total). The HCP concentration was reduced to 144 ng/mL (5.3×10$^4$ ng total) for at least a 1.7 log reduction in total HCP prior to purification. The rDNA concentration measured in the in the batch lysate yielded 5053.9 ng/mL (1.8×10$^7$ ng total). Following purification, the rDNA concentration was reduced to 4169.9 ng/mL (1.5×10$^6$ ng total) for a 1.1 log reduction in total rDNA.

Testing Methods:

Endotoxin content was measured using the LAL endotoxin kit (described above).

Host cell protein content was measured using Cygnus Technologies S. aureus Host Cell Proteins ELISA Kit (F320) following the manufacturer's protocol. Quality control samples are included in each HCP test to ensure the run provides accurate results (product spike control, a zero standard and S. aureus Host-Cell Protein standards).

Residual DNA content was determined by Quant-It High Sensitivity (Quant-It HS) and Quant-It Broad Range (Quant-it BR) fluorescent probes (ThermoFisher Scientific) following the manufacturer's protocol. The sample from the bulk material was pre-filtered with 0.22 um filters and washed on a 100 kDa MWCO Amicon filter to remove digested fragments of residual host cell DNA and resuspended in PBS prior to reading the sample. Purified phage material was not washed in the Amicon filter process prior to measuring the rDNA concentration.

TABLE 3

| Bacteriophage Strain | Phage Morphology/Family | Subfamily[5] | Dimensions Length (nm) | Width (nm) | Host Bacteria Genus | Species |
|---|---|---|---|---|---|---|
| AbTB41Φ165[3] | Podoviridae | unknown | 69 ± 3 | 51 ± 5 | Acinetobacter | baumannii |
| Ax2CJ45Φ2[3] | Podoviridae | unknown | 65 ± 1 | 51 ± 1 | Achromobacter | xylosoxidans |
| AxII45EH42Φ1[3] | Siphoviridae | unknown | 203 ± 13 | 54 ± 2 | Achromobacter | xylosoxidans |
| EcCH27Φ38[1,3] | Podoviridae | Autographivirinae | 73 ± 4 | 59 ± 3 | Escherichia | coli |
| EcCH79Φ79[1,3] | Podoviridae | Autographivirinae | 74 ± <1 | 55 ± 2 | Escherichia | coli |
| EcCH54Φ54[2] | Myoviridae | Tevenvirinae | unknown | unknown | Escherichia | coli |
| EcCH58Φ58[2,3] | Myoviridae | unknown | 203 ± 5 | 79 ± 3 | Escherichia | coli |
| EcCH74Φ74[2,3] | Myoviridae | Tevenvirinae | 195 ± 5 | 74 ± 2 | Escherichia | coli |
| EcCH16Φ26[2] | Podovirdae | Autographivirinae | unknown | unknown | Escherichia | coli |
| EcCH17Φ27[2] | Podoviridae | Autographivirinae | unknown | unknown | Escherichia | coli |
| EcCH94Φ94[2] | Podoviridae | Autographivirinae | unknown | unknown | Escherichia | coli |
| EcCH53Φ53[2] | Podoviridae | Autographivirinae | unknown | unknown | Escherichia | coli |
| EcCH56Φ56A[2] | Myoviridae | Tevenvirinae | unknown | unknown | Escherichia | coli |
| EcCH111Φ111[2] | Podoviridae | Autographivirinae | unknown | unknown | Escherichia | coli |
| EcCH63Φ63A[2] | Myoviridae | Vequintavirinae | unknown | unknown | Escherichia | coli |
| KpC42Φ1[2,3] | Siphoviridae | unknown | 200 ± | 61 ± 3 | Escherichia | coli |
| KpC53Φ2[2] | Siphoviridae | unknown | unknown | unknown | Klebsiella | pneumoniae |
| KpKH52Φ07B | Unknown | unknown | unknown | unknown | Klebsiella | pneumoniae |
| KpJH46Φ2 | Unknown | unknown | unknown | unknown | Klebsiella | pneumoniae |
| SaWIQ0456AΦ1 | Unknown | unknown | unknown | unknown | Staphylococcus | aureus |
| SeMN68Φ1 | Unknown | unknown | unknown | unknown | Staphylococcus | epidermidis |
| SaWIQ0488Φ1[2] | Podoviridae | Picovirinae | unknown | unknown | Staphylococcus | aureus |
| SaGR51ΦK1[4] | Myoviridae | unknown | unknown | unknown | Staphylococcus | aureus |
| Pa14NPΦPASA16[3] | Myoviridae | unknown | 189 ± 20 | 66 ± 3 | Pseudomonas | aeruginosa |
| PaGJ50BΦ117 | Unknown | unknown | unknown | unknown | Pseudomonas | aeruginosa |
| PaGJ50AΦ141 | Unknown | unknown | unknown | unknown | Pseudomonas | aeruginosa |

[1] Phage strains have been amplified multiple times
[2] Morphology prediction via bioinformatic analysis
[3] Morphology determined from TEM imaging
[4] Morphology known from literature sources
[5] Subfamily is based on bioinformatic analysis Example 4, 5 and 6

Recovery of Kp531Φ2 KpKH52Φ07B and EcCH56Φ56A from Large Scale Cultures with Multiple Cycles of Purification Batch to batch variation in the concentration of process derived contaminants (bacterial Endotoxins, Host Cell Proteins, etc.) could require reprocessing to achieve the desired results. This can be especially true when amplifying and purifying different phages in different host bacterial species and/or strains requiring an operator to compensate for these changes in the system. The invention has demonstrated flexibility in that the material may be reprocessed using the same method(s) or a combination of methods until the contaminants have been reduced to a desired level while preserving bacteriophage titer. Three examples of successful reprocessing of material have been provided below:

Examples 4 and 5

Kp531Φ2 and KpKH52Φ07B

Two Klebsiella phages, Kp531Φ2 and KpKH52Φ07B were amplified in separate batch cultures and bulk contaminants removed via centrifugation followed by sequential filtration through 0.88 um, 0.45 um, and 0.22 um. The prefiltered Kp531Φ2 and KpKH52Φ07B batches, were both loaded into a processed through the purification in a TFF flow path equipped with a 300 kDa MWCO hollow fiber filter. Specifically, each batch was concentrated ~10×, subjected to 4 DV washes with 500 mM in NaCl, 2 DV washes with 0.1% Triton X-100, 4 DV washes with 1×PBS, 2 DV washes with Triton X-100, 4 washes with 1×PBS, followed by 3 DV washes with $(NH_4)_2SO_4$, followed by 10×DV washes with 1×PBS. The purified material was then loaded into a second filtration flow path equipped with a 100 kDa MWCO hollow fiber filter and washed with 10 DV of injection grade excipient to further remove residual salts and/or detergents from the purification buffers. The purified material is then concentrated and tested for residual contaminants.

After processing, the phage titer and endotoxin content was tested for both the Kp531Φ2 and KpKH52Φ07B batches. Both batches had a high phage titer, Kp531Φ2 at $1.9 \times 10^9$ PFU/mL and KpKH52Φ07B at $1.4 \times 10^{11}$ PFU/mL, but also tested high in endotoxin content, Kp531Φ2 at 9,138 EU/mL and KpKH52Φ07B at 83,600 EU/mL. Due to the high endotoxin content, the both batches were re-processed through the purification process a second time and followed up with a second polish step. After reprocessing the endotoxin content for Kp531Φ2 and KpKH52Φ07B was 565 EU/mL and 488 EU/mL respectively. Additionally, Kp531Φ2 and KpKH52Φ07B both maintained a high titer $7.3 \times 10^9$ PFU/mL and $1.0 \times 10^{11}$ PFU/mL respectively.

Example 6

EcCH56Φ56A

An *E. coli* phage batch, EcCH56Φ56A, was amplified in a batch culture and bulk contaminants removed via centrifugation followed by sequential filtration through 0.88 μm, 0.45 μm, and 0.22 μm. The prefiltered material, was a processed through the purification in a TFF flow path equipped with a 300 kDa MWCO hollow fiber filter. Specifically, the batch was concentrated ~10×, subjected to 4 DV washes with 500 mM NaCl, 2 DV washes with 0.1%

Triton X-100, 4 DV washes with 1×PBS, 2 DV washes with Triton X-100, 4 washes with 1×PBS, followed by 3 DV washes with $(NH_4)_2SO_4$, followed by 10×DV washes with 1×PBS.

After purification, the batch was tested for phage titer as well as endotoxin content. The batch maintained a high phage titer, $1.2\times10^{10}$ PFU/mL, but was also high in endotoxin content, 52,745 EU/mL. Due to the high endotoxin content, the EcCH56phi56A batch was re-processed through the purification process a second time. The titer yielded $6.8\times10^{10}$ PFU/mL after the second purification run. It was then followed up with a polish step in which the purified material was then loaded into a second filtration flow path equipped with a 100 kDa MWCO hollow fiber filter and washed with 10 DV of injection grade excipient to further remove residual salts and/or detergents from the purification buffers and prepare phage for therapeutic use. After reprocessing, the endotoxin content for EcCH56Φ56A was 30 EU/mL and maintained a high titer of $5.2\times10^{10}$ PFU/mL.

The invention is not limited to the embodiment herein before described which may be varied in construction and detail without departing from the spirit of the invention. The entire teachings of any patents, patent applications or other publications referred to herein are incorporated by reference herein as if fully set forth herein.

What is claimed:

1. A method of recovering viable phage from a crude phage preparation, wherein the method comprises the steps of:
   a) adding the crude phage preparation to Tangential Flow filtration system comprising a size exclusion filter, wherein said filter comprises a pore size smaller than a size of the phage contained within the crude phage preparation;
   b) passing a series of buffers over the filter, wherein said series of buffers comprise, in any order:
   1) A buffer that disrupts ionic protein interactions, wherein said buffer comprises sodium chloride and/or magnesium chloride at a concentration in the range of 250-950 mM;
   2) A buffer comprising a detergent in a concentration sufficient to disrupt hydrophobic/hydrophilic interactions, wherein said detergent is a polyoxyethylene derivative and/or a zwitterionic surfactant; and
   3) A buffer at a concentration that precipitates the phage without denaturing the phase; wherein said buffer comprises a salt selected from the group consisting of ammonium sulfate, sodium sulfate and magnesium sulfate;
   wherein one or both of steps 1) and 2) optionally may be repeated; and
   c) recovering said phage from the filter, wherein said recovered phage are viable.

2. The method of claim 1, wherein the pore size permits passage of materials of a size less than 100 Kda, less than 150 Kda, less than 200 Kda, less than 250 Kda, less than 300 Kda, less than 350 kDa, less than 400 kDa, less than 450 KDa, less than 500 kDa, less than 550 kDa, less than 600 kDa, less than 650 kDa, less than 700 kDa, less than 750 kDa, or less than 800 kDa.

3. The method of claim 1, wherein the size exclusion filter is a hollow fiber filter.

4. The method of claim 1, wherein:
   the buffer that precipitates the phage is an ammonium sulfate buffer.

5. The method of claim 4, wherein the buffer that disrupts ionic protein interactions comprises 500 to 650 mM sodium chloride.

6. The method of claim 1, wherein the buffer that disrupts hydrophobic/hydrophilic interactions comprises:
   (i) Triton X-100;
   (ii) Triton X-100 and a second detergent;
   (iii) Triton X-100 and a high ionic strength solution wherein said solution comprises sodium chloride and/or magnesium chloride at a concentration in the range of 250-950 mM; or
   (iv) Triton X-100 and a chaotropic agent.

7. The method of claim 1, wherein the method further comprises one or more wash step(s) between passing any or all of buffers 1), 2) and 3) over the filter in step b).

8. The method of claim 1 wherein the buffers in step b) are passed over the filter in the order 1), 2) and 3).

9. The method of claim 1, wherein the method further comprises adding an endonuclease selected from the group consisting of a DNAase, a RNAase and benzonase.

10. The method of claim 9, wherein said endonuclease is added to the crude phage preparation.

11. The method of claim 9, wherein said endonuclease is added to the recovered phage in solution.

12. The method of claim 1, wherein the recovered viable phage is further subjected to a centrifugation step.

13. The method of claim 1, further comprising a pre-processing step where the crude phage preparation is pre-processed to remove large contaminants, wherein the pre-processing step comprises centrifugation, and/or filtration through a porous filter membrane or other size exclusion filter and/or depth filter, or a perfusion technique.

14. The method of claim 1, wherein the recovered viable phage has an endotoxin titer of less than 1 EU/ml, less than 100 EU/ml, less than 200 EU/ml, less than 300 EU/ml, less than 400 EU/ml, less than 500 EU/ml, less than 600 EU/ml, less than 700 EU/ml, less than 800 EU/ml, less than 900 EU/ml, or less than 1000 EU/ml.

15. The method of claim 1, wherein the recovered viable phage has a titer of greater than $0.5\times10^8$ PFU/ml, of greater than $1\times10^8$ PFU/ml, of greater than $0.5\times10^9$ PFU/ml, or of greater than $1\times10^9$ PFU/ml.

16. The method of claim 1, wherein host cell protein levels in the recovered viable phage are less than or equal to 100 μg/mL.

17. The method of claim 1, wherein the method further comprises exchanging the buffer of the recovered viable phage with a pharmaceutically acceptable buffer suitable for administration to a patient.

18. The method of claim 17, wherein the buffer is suitable for IV administration.

19. A method of recovering viable phage from a crude phage preparation, comprising:
   a) adding the crude phage preparation to a tangential flow filtration system comprising a size exclusion filter, wherein said filter comprises a pore size smaller than the size of the phage in the crude phage preparation;
   b) washing the resulting lysate with a high ionic strength buffer that disrupts ionic protein interactions, wherein said buffer comprises 250-950 mM sodium chloride;
   c) washing the resulting lysate with a buffer comprising Triton X-100 in a concentration sufficient to disrupt hydrophobic/hydrophilic interactions;
   d) washing the resulting lysate with a buffer comprising ammonium sulfate at a concentration that precipitates the phage without denaturing the phage; and
   e) recovering said viable phage from the filter.

* * * * *

UNITED STATES PATENT AND TRADEMARK OFFICE
CERTIFICATE OF CORRECTION

PATENT NO. : 12,006,517 B2
APPLICATION NO. : 17/571645
DATED : June 11, 2024
INVENTOR(S) : Joseph Robert Fackler et al.

It is certified that error appears in the above-identified patent and that said Letters Patent is hereby corrected as shown below:

In the Claims

Claim 1, Column 21, Line 47, replace "without denaturing the phase; wherein said buffer" with --without denaturing the phage; wherein said buffer--

Signed and Sealed this
Seventeenth Day of September, 2024

Katherine Kelly Vidal
*Director of the United States Patent and Trademark Office*